United States Patent [19]

Kamen et al.

[11] Patent Number: 4,938,952
[45] Date of Patent: Jul. 3, 1990

[54] POLYMER SUPPORTED COSMETIC PRODUCTS AND METHODS

[75] Inventors: Melvin E. Kamen, Highlands; Philip Bernstein, Glen Ridge; Amit R. Shah, Iselin, all of N.J.

[73] Assignee: Revlon, Inc., New York, N.Y.

[21] Appl. No.: 258,219

[22] Filed: Oct. 14, 1988

[51] Int. Cl.$^5$ .................. A61K 7/021; A61K 7/027; A61K 7/032
[52] U.S. Cl. ............................... 424/63; 424/64; 424/69; 424/78
[58] Field of Search .................. 424/63, 64, 83, 486, 424/69, 489, 501, 78, 901

[56] References Cited

U.S. PATENT DOCUMENTS

| | | | |
|---|---|---|---|
| 4,332,698 | 6/1982 | Bernstein et al. | 502/4 |
| 4,358,396 | 11/1982 | Bernstein et al. | 502/159 |
| 4,396,693 | 8/1983 | Bernstein et al. | 429/217 |
| 4,433,063 | 2/1984 | Bernstein et al. | 502/402 |
| 4,659,562 | 4/1987 | Arraudeau et al. | 424/64 |

*Primary Examiner*—Ellis P. Robinson
*Assistant Examiner*—Susan S. Rucker

[57] ABSTRACT

A cosmetic product includes a cosmetic component as a pigment maintained within a matrix of fibrillatable polymer. The pigment and polymer composition provides a cosmetic which can be employed for coloration of the skin and utilized as eye makeup, powder, or other cosmetic products by employing suitable processing techniques as extrusion, milling, compacting and so on.

22 Claims, No Drawings

4,938,952

POLYMER SUPPORTED COSMETIC PRODUCTS AND METHODS

BACKGROUND OF THE INVENTION

This invention relates to cosmetics in general and more particularly to a product incorporating a cosmetic component supported in a fibrillated polymer matrix.

Cosmetics have been used since early times to beautify the skin and hair. The manufacture of cosmetics is a 20th century development under the influence of Hollywood in the 1920's coupled with the development of mass production and mass marketing techniques. As a consequence, cosmetics were offered to the public at cheap prices. As one can ascertain, the cosmetic industry today is huge and there are a tremendous number of products utilized.

While most cosmetics are relatively simple, they contain many ingredients which are employed to formulate the various cosmetic preparations. Essentially a cosmetic chemist uses a variety of materials which are often based on emulsified mixtures of oils, water or water soluble products, pigments, talcs and so on.

Manufacturing processes of cosmetics can normally be divided into three main lines, as lipsticks and related sticks, creams and lotions, and compressed powders, as for example cake makeup. This application relates to compressed powder type of cosmetics, but is applicable to other cosmetic products as well.

In the prior art compressed powders were also referred to as cake makeup and are widely employed because of their ease of application and stability and also because they adhere to the skin easily. The most well known is a compressed face powder which usually is made from a mixture of talc, kaolin, zinc oxide and precipitated chalk. It also includes lanolin derivatives, wax and pigment such as titanium and iron oxides. The liquid constituents, including a humectant and perfume are sprayed into the powder while it is in a ribbon mixer. The product is milled to make it homogenous and left to stand to allow air that has been entrained to escape and then pressed by one or more stages employing pressures between 200-250 psi to form a cake.

Cake eye shadows contain about 60% talc and an emollient which is a skin softening agent which allows the cake to be transferred by pressing out. Approved pigments are also added as for example a black coloration being provided by iron oxide. Eye shadows of a metallic luster use finely ground metal such as aluminum or natural or synthetic pearlized materials. The formulation of such cosmetic products comprises a great deal of material including fairly extensive labor processes as well as other time consuming operations.

It is indicated that the dispersion of pigments in cosmetics may require different materials as above indicated and many different steps in order to provide the final product. These steps usually take an extreme amount of time and are labor and capital intensive.

It is an object of the present invention to provide a simple and efficient cosmetic which essentially contains a cosmetic component as a pigment supported by a polymer matrix.

As one will ascertain from the prior art, certain polymers, such as for example Teflon, possess a property called fibrillation. The use of fibrillatable polymers is well known in the prior art. Such polymers have been employed to support various elements and can disperse with such elements as such polymers are relatively non-reactive with the environment into which it's been used. Fluorocarbon and polypropylene polymers have such suitable characteristics and are capable of being fibrillated. As will be further explained, the term fibrillation means that such polymers, when exposed to pressure and/or heat, explode producing fibrils or minute fibers. These fibers are minute fiber particles which are developed in situ from the fibrillatable polymers during processing. As such the fibrils intermesh in a matrix-like form and are used with other components to provide various products.

For examples of prior art techniques using fibrillatable polymers, reference is made to the following U.S. patents. See U.S. Pat. No. 4,332,698 issued on June 1, 1982 and entitled "Catalyst Sheet And Preparation" by P. Bernstein, et al. This patent shows techniques employing fibrillatable polymers. U.S. Pat. No. 4,358,396 issued on Nov. 9, 1982 and entitled "Particulate Catalyst And Preparation" to P. Bernstein, et al. shows additional techniques. See U.S. Pat. No. 4,396,693 issued on Aug. 2, 1983 and entitled "Production Of A Cell Electrode System" by P. Bernstein, et al. See U.S. Pat. No. 4,433,063 issued on Feb. 21, 1984 and entitled "Hydrogen Sorbent Composition" by P. Bernstein, et al.

As indicated, the above patents are some examples of the use of fibrillatable materials which operate in conjunction with various compositions.

In any event, it has been determined that the use of a fibrillatable polymer in conjunction with a cosmetic pigment produces a cosmetic article or product which has extremely desirable characteristics, such as a tendency to be water resistant, a smooth silky feeling when applied to the skin of the user, extreme sheen, non-abrasive qualities and overall a superior cosmetic product as compared to prior art products as above indicated.

SUMMARY OF THE INVENTION

A cosmetic product comprising a matrix of a fibrillated polymer supporting at least one cosmetic pigment.

DETAILED DESCRIPTION OF THE INVENTION

It is believed that this specification does not require drawings as the products and compositions are adequately described and understood.

As indicated, this invention employs a fibrillatable polymer in conjunction with a cosmetic component as a pigment to produce a cosmetic product having superior qualities. The fibrillatable polymer is compatible with the pigment and is capable of dispersing in it and is totally non-reactive with both the pigment and the environment in which it is to be used. The combination of the polymer and pigment can provide cosmetic products which can be processed using pressing, extruding and various other techniques to produce a wide range of different products, all of which can impart a desired color to the skin. The product, by the use of a polymer such as Teflon, is extremely smooth, lubricious, simple, and inexpensive. It is immediately ascertained that the product essentially comprises a given percentage of a fibrillatable polymer in conjunction with a pigment and will have all the properties of prior art cake-type cosmetics with many advantages.

As is known, fluorocarbon and polypropylene polymers have the capability of fibrillation. According to the techniques of the present invention, it is advantageous for the polymer to be fibrillatable in a dry-type process. In any event, such polymers are known. For example, polytetrafluoroethylene (PTFE) can be fibrillated from a dry powder and is commercially available as duPont's Teflon 6A and 7A. Fibrillatable polypropylene is available for example as strands, tapes or films which can be used as such or chopped to appropriate sizes.

As will be further understood, according to the techniques of the present invention these fibrillatable polymers are employed as a support for a cosmetic component as a pigment. The fibrillatable polymer, when fibrillated, explodes into strands or fibers into which strands are enmeshed the cosmetic pigment. The cosmetic pigment is held in intimate contact with the polymer and can be applied to the skin together with the polymer to provide a unique type of cosmetic product. The strands of fiber intermesh to form a support matrix which encloses and surrounds the cosmetic component.

As indicated, polytetrafluoroethylene (PTFE) is a fluorocarbon resin which undergoes the phenomenon known as fibrillation when the PTFE powder is exposed to shear. This is done with an extreme change in temperature or change in its pH environment. For example, duPont manufactures a PTFE as Teflon 7A which is a powder of high bulk density usually used to mold large shapes. It has been discovered that when Teflon 7A is placed in a high shear mixer, such as a Waring blender, and mixed for two minutes, the powder is converted to a fibrillated mass. When these fibers are compacted they hold the shape of any container in which they were compressed. Thus one can make a mixture of pigment and the fibrillated Teflon in 5%, 10% and 20%concentrations of Teflon 7A with a suitable pigment or cosmetic component.

The pigments employed are cosmetic pigments widely used for coloration and for example such pigments can be ultramarine violet-3516 iron oxide, metallic pigments and so on. In one case 9 grams of ultramarine violet-3516 was blended with 1 gram of Teflon 7A (PTFE) for two minutes in an IKA-WERK miniblender at room temperature. During the mixing the blender was inverted or shaken a number of times to insure complete mixing of the PTFE with the pigment. The pigment coated PTFE was taken from the blender and pressed into an eye shadow pan. The formulation containing only the two components with 90% of the pigment and 10% of the Teflon held the shape of the pan, had a silky feeling and showed an extremely good payoff.

Other processing techniques will operate as well such as milling, extruding and injection molding of the fibril supported pigments. Milling the pigment and PTFE combination produces sheets of materials which are then die cut into various shapes. One can also extrude the mixture to obtain cylinders of material which are cut into various desired lengths for cosmetic pencils, sticks and so on. The mixture can be pelletized to provide cosmetic pellets for skin coloration or other purposes. The fibril supported pigment has applications in conjunction with various other cosmetic products, such as lipsticks, eye shadows, eye liners, creams and other cosmetics and toiletries. It is of course understood that a perfume or fragrance can be added to the pigment supported polymer to impart a desired fragrance to the same. It is understood that other polymers which are capable of fibrillation, such as polypropylene and so on, can also be used.

As one can ascertain from the above, the processing techniques are extremely simple as utilizing a mechanical blending process whereby based on the nature of the polymer there are no binders necessary, there is no talc necessary and the resulting product is extremely smooth to the feel and is capable of easy and smooth application. The combination of pigment and Teflon fibers can be extruded to produce for example Teflon sheets which sheets can then be cut by means of die cutting techniques to provide various cosmetic shapes which will impart the pigment color to the skin of a user as well as the PTFE fibers. Thus, the product can be extruded, milled, compression or injection molded while it maintains integrity and isolation.

It is further understood that the product is relatively hydrophobic or waterproof due to the properties of PTFE and hence the product is relatively water resistant as compared to other cosmetic formulations. One can employ any of the conventional cosmetic pigments, such as iron oxides and the same types of pigments which are presently utilized in pressed caked techniques or for cosmetic preparations. The amount of PTFE employed is between 1-25% by weight of the product with the remainder being a cosmetic component or a pigment. These percentages can be varied accordingly and according to the particular product desired. Hence, one may include as much as 50% of the polymer together with 50% of pigment and additional fragrances as so desired.

The cosmetic product is relatively stick free, water resistant and, as indicated, completely eliminates the necessity for any binder to be utilized. Thus, as one can ascertain, the product consists completely of a cosmetic component as pigment and the polymer fibrils and need not include any additional cosmetic components as binders, oils and so on.

It is of course understood that the polymer can be utilized together with some talc and pigments as other cosmetic components and one can compress the mixture and mold the mixture in any particular manner desired. For example, the material can be fabricated into sticks employing a ram extrusion technique which essentially compacts the material in a cylinder and then a dye is used to force the material out of the cylinder through a suitable aperture. The combination pigment and polymer has the appearance of a cylinder of colored cosmetic material or appears as a piece of colored chalk. This cosmetic product can be applied directly to the skin and exhibits an extremely smooth feeling while having all the attributes as indicated above.

What is claimed is:

1. A cosmetic product comprising a matrix of a fibrillated polymer supporting at least one cosmetic pigment.

2. The cosmetic product according to claim 1 wherein said fibrillated polymer is polytetrafluoroethylene (PTFE).

3. The cosmetic product according to claim 1 wherein said fibrillated polymer is a polypropylene.

4. The cosmetic product according to claim 1 wherein said cosmetic pigment is iron oxide.

5. The cosmetic product according to claim 1 wherein said pigment is ultramarine violet.

6. The cosmetic product according to claim 1 wherein said product comprises between 1-25% by weight of said polymer with the remainder being said cosmetic pigment.

7. The cosmetic product according to claim 1 including 10% by weight of said polymer and 90% of said cosmetic pigment.

8. A method of forming a cosmetic product comprising the steps of:
   subjecting a fibrillatable polymer to high shear forces to cause said polymer to fibrillate;
   adding a cosmetic pigment to said fibrillated polymer;
   mixing said fibrillated polymer with said cosmetic pigment; and
   processing said mixed polymer and cosmetic pigment to form a cosmetic product.

9. The method according to claim 8 wherein the step of processing includes pressing said mixed polymer and cosmetic pigment into a suitable container.

10. The method according to claim 8 wherein the step of processing includes extruding said mixed polymer and cosmetic pigment into cylindrical cosmetic configurations.

11. The method according to claim 8 wherein said polymer is polytetrafluoroethylene (PTFE).

12. The method according to claim 8 wherein said polymer is polypropylene.

13. The method according to claim 8 employing between 1-25% of said polymer by weight with the remainder being said cosmetic pigment.

14. The method according to claim 8 wherein said pigment is ultramarine violet.

15. The method according to claim 8 wherein said pigment is iron oxide.

16. The method according to claim 8 employing 90% by weight of said polymer and 10% of said cosmetic pigment.

17. The method according to claim 8 wherein the step of subjecting said polymer includes placing said polymer in a high shear mixer and mixing said polymer for a given period sufficient to cause fibrillation.

18. The method according to claim 8 wherein said polymer is in a powder form.

19. The method according to claim 8 wherein said pigment comprises 90% by weight of the mixture.

20. The method according to claim 19 wherein the step of processing includes pressing said mixture into an eye shadow pan.

21. A method of forming a cosmetic product comprising the steps of:
   subjecting a fibrillatable polymer to high shear forces to cause said polymer to fibrillate,
   adding a cosmetic pigment to said fibrillated polymer,
   milling said mixed polymer and cosmetic pigment into sheets; and
   forming a cosmetic product of a given configuration from said sheets.

22. The method according to claim 21 including the further step of cutting said planar sheets into a desired configuration is carried out by means of a die.

* * * * *